United States Patent [19]
Kohayakawa

[11] Patent Number: 5,889,577
[45] Date of Patent: *Mar. 30, 1999

[54] OPTICAL APPARATUS OR APPARATUS FOR DETECTING DIRECTION OF LINE OF SIGHT, AND VARIOUS KINDS OF SAME APPARATUS USING THE SAME

[75] Inventor: Yoshimi Kohayakawa, Yokohama, Japan

[73] Assignee: Canon Kabushiki Kaisha, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 917,699

[22] Filed: Aug. 26, 1997

Related U.S. Application Data

[63] Continuation of Ser. No. 383,693, Feb. 1, 1995, abandoned, which is a continuation of Ser. No. 890,076, May 29, 1992, abandoned.

[30] Foreign Application Priority Data

| May 31, 1991 | [JP] | Japan | 3-157628 |
| May 31, 1991 | [JP] | Japan | 3-157629 |
| Jun. 26, 1991 | [JP] | Japan | 3-180451 |
| May 26, 1992 | [JP] | Japan | 4-160228 |

[51] Int. Cl.$^6$ .................................................. A61B 3/10
[52] U.S. Cl. ..................... 351/211; 351/208; 351/237; 351/243; 351/221
[58] Field of Search .................................. 351/204, 206, 351/208, 211, 212, 214, 221, 224, 237, 243, 247

[56] References Cited

U.S. PATENT DOCUMENTS

| 4,372,655 | 2/1983 | Matsumura et al. | 351/206 |
| 4,650,300 | 3/1987 | Joncour | 351/204 |
| 4,836,670 | 6/1989 | Hutchinson | 351/210 |
| 5,114,222 | 5/1992 | Cornsweet | 351/204 |
| 5,225,862 | 7/1993 | Nagano et al. | 354/62 |
| 5,428,413 | 6/1995 | Shindo | 351/210 |
| 5,486,892 | 1/1996 | Suzuki et al. | 396/271 |

FOREIGN PATENT DOCUMENTS

61-59132  12/1986  Japan.

*Primary Examiner*—Scott J. Sugarman
*Attorney, Agent, or Firm*—Fitzpatrick, Cella, Harper & Scinto

[57] ABSTRACT

An optical apparatus includes a pupil illuminator for illuminating the pupil of an eye of an individual, an imager for obtaining an image of the pupil and an image of the cornea of the eye, a presentor for preliminarily presenting an image positioned at a particular point to the eye, and a direction-of-line-of-sight calculator for calculating the direction of the line of sight of the eye using the positional relationship between the image of the pupil and the image of the cornea on an imaging surface of the imager, and calculating the direction of the line of sight using parameters relating to the image of the pupil and the image of the cornea. The values of the parameters are obtained from the positional relationship between the image of the pupil and the image of the cornea on the imaging surface of the imager when the eye views the image at the particular point.

21 Claims, 9 Drawing Sheets

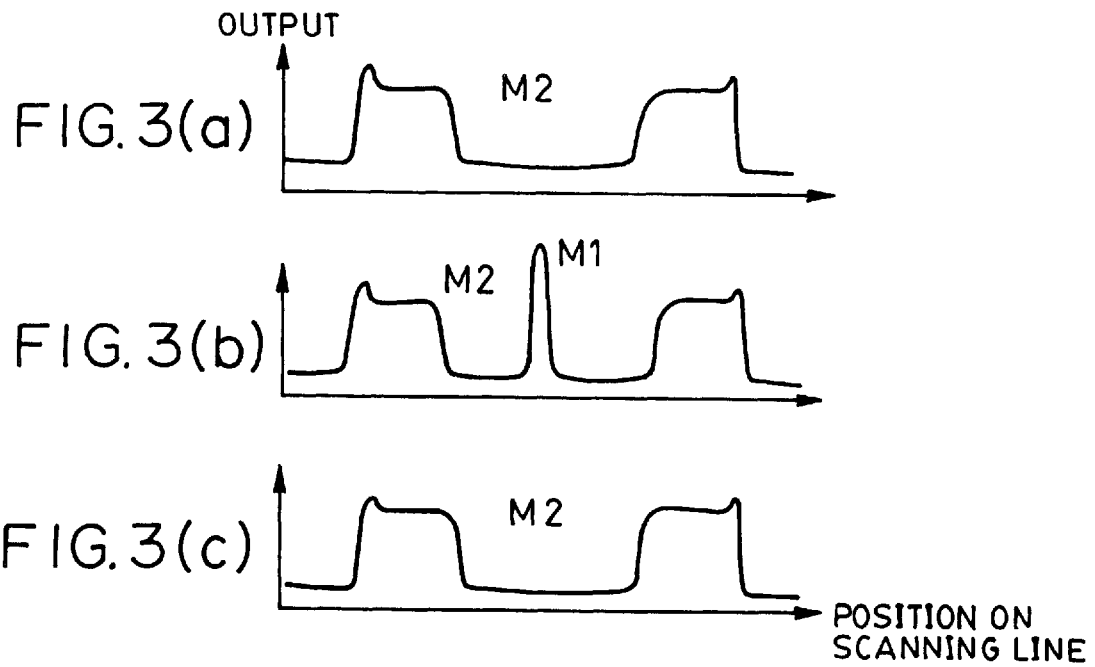
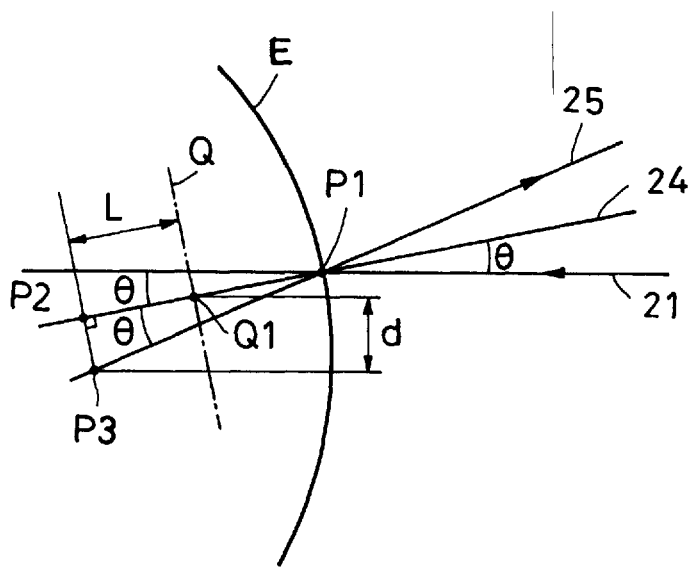

OPTICAL APPARATUS OR APPARATUS FOR DETECTING DIRECTION OF LINE OF SIGHT, AND VARIOUS KINDS OF SAME APPARATUS USING THE SAME

This application is a continuation of application Ser. No. 08/383,693 filed Feb. 1. 1995 now abandoned, which is a continuation of application Ser. No. 07/890,076, filed May 29, 1992, abandoned.

BACKGROUND OF THE INVENTION

1. Field of the Invention

This invention relates to an optical apparatus or an apparatus for detecting the direction of the line of sight of an eye, and various kinds of apparatuses using the same.

2. Description of the Related Art

In some of conventional apparatuses for detecting the direction of the line of sight of an eye, first and fourth Purkinje images are utilized, or the positional relationship between light beams reflected by the cornea of the eye, and the pupil of the eye is utilized.

However, in the above-described conventional approach utilizing Purkinje images, since the amount of received light of the fourth image is small, it is difficult to perform detection. In the approach simply utilizing only the relative relationship between light reflected by the cornea of an eye, and the pupil of the eye, detection accuracy is low because the relationship between the images of the cornea and the pupil varies with the individual. Hence, this approach can be used only for monitoring whether or not the direction of the line of sight of an eye is within a certain range.

In conventional perimeters, stimulating light is presented at a particular point near the line of sight of a person to be tested while the line of sight is fixed onto a fixed lamp, and the field of view of the person is measured according to whether or not the stimulating light can be seen. Such a perimeter usually includes a means for monitoring the line of sight of an eye since an error of measurement is produced if the fixed lamp is out of the line of sight of the person. For example, as disclosed in Japanese Patent Publication No. 61-59132 (1986), the direction of the line of sight is measured from the positional relationship between the image of light beams reflected by the cornea of an eye, and the pupil of the eye, and remeasurement is generally performed if the fixed lamp is out of the line of sight.

In the above-described conventional approach, however, since it is very difficult for an eye to be tested to continue to watch the fixed lamp, the line of sight of the eye shifts during measurement, causing an error of measurement of the field of view. Hence, remeasurement is performed if the fixed lamp is out of the line of sight, causing an increase in the time of measurement. As described above, detection accuracy is low using the method of detecting the direction of line of sight from the relationship between the image of light beams reflected by the cornea of an eye, and the image of the pupil of the eye. Hence, this approach can be used only for monitoring whether or not the direction of the line of sight is within a certain range.

In conventional focus apparatuses which can be applied to video cameras, slit lamps, operation microscopes and the like, if a focus sensor is used, the focus sensor is mounted so as to perform a focus operation on a particular position on the picture frame. In another approach, an object is picked up by an image pickup device, and a focus operation is performed using a video signal from the image pickup device.

However, in using a focus sensor aiming at a particular position on the picture surface, if a portion the operator desires to be focused is out of the particular position, this portion is not always focused. In performing a focus operation using a video signal, the desired portion is not always focused since a light portion having a high contrast is focused.

SUMMARY OF THE INVENTION

It is an object of the present invention to overcome the problems of the prior art.

It is another object of the present invention to provide an optical apparatus or an apparatus for detecting the direction of the line of sight of an eye which can detect the direction of the line of sight of the eye with high precision irrespective of the relationship between the images of the cornea and the pupil, which vary for different individuals.

It is a still futher object of the present invention to provide various kinds of apparatuses which can use the above-described apparatus for detecting the direction of the line of sight of the eye.

It is a still another object of the present invention to provide a perimeter in which it is unnecesary for an eye to be tested to continuously view a fixed lamp, and with which the direction of the line of sight can be precisely detected.

It is still another object of the present invention to provide a focus apparatus which automatically focuses on a portion on a display means to which the line of sight of the eye is directed.

According to one aspect, the present invention which achieves these objectives relates to an optical apparatus comprising pupil illuminating means for illuminating the pupil of an eye of an individual, imaging means for obtaining an image of the pupil illuminated by the pupil illuminating means and an image of the cornea of the eye composed of light reflected by the cornea of the eye, presenting means for preliminarily presenting an image positioned at a particular point to the eye, and direction-of-line-of sight calculation means for calculating the direction of the line of sight of the eye. The direction-of-line-of-sight calculation means calculates the direction of the line of sight of the eye using the positional relationship between the image of the pupil and the image of the cornea, composed of light reflected by the cornea, on an imaging surface of the imaging means and calculates the direction of the line of sight using parameters relating to the image of the pupil and the image of the cornea, the values of which vary for different individuals. The values of the parameters are obtained from the positional relationship between the image of the pupil and the image of the cornea, composed of light reflected by the cornea, on the imaging surface of the imaging means when the eye views the image at the particular point.

The apparatus further comprises field-of-view measuring means for presenting stimulating light beams at one point in the field of view of the eye, and measuring the field of view of the eye by obtaining information on when the stimulating light beams are in the field of view from the individual to be tested, while moving the position of the stimulating light beams within the field of view.

The apparatus further comprises projection means for projecting the image of an object and display means for displaying the image of the object to present the image of the object to the individual. The projection means comprises focus means for performing a focus operation according to a focus state of the projection means. The direction-of-lineof-sight calculation means calculates the direction of the line of sight while the individual observes the display means. The focus means performs a focus operation according to a focus state of the projection means with respect to a portion of the object corresponding to a portion of the image of the object on the display means present the calculated direction of the line of sight of the individual.

The apparatus can obtain information on strabismus of the individual according to a result of the calculation by the direction-of-line-of-sight calculation means.

According to another aspect, the present invention which achieves these objectives relates to a direction-of-line-of-sight detecting means comprising pupil illuminating means for illuminating the pupil of an eye of an individual, imaging means for obtaining an image of the pupil illuminated by the pupil iluminating means and an image of the cornea of the eye composed of light reflected by the cornea of the eye, presenting means for preliminarily presenting an image positioned at a particular point to the eye, and direction-of-line-of-sight calculation means for calculating the direction of the line of sight of the eye. The direction-of-line-of-sight calculation means calculates the direction of the line of sight using the positional relationship between the image of the pupil and the image of the cornea, composed of light reflected by the cornea, on an imaging surface of the imaging means, and calculating the direction of the line of sight using parameters relating to the image of the pupil and the image of the cornea, composed of light reflected by the cornea, the values of which vary for different individuals. The values of the parameters are obtained from the positional relationship between the image of the pupil and the image of the cornea, composed of light reflected by the cornea, on the imaging surface of the imaging means when the eye views the image at the particular point.

The apparatus can further comprise a system for playing a television game, the system operating according to a result of the calculation of the direction-of-line-of-sight calculation means.

According to still another aspect, the present invention which achieves these objectives relates to a perimeter comprising a field-of-view measuring system for presenting stimulating light beams to one point in the field of view of the eye of an individual to be tested, and measuring the field of view according to information on when the stimulating light beams are in the field of view obtained from the individual while moving the point at which the sitmulating light beams are presented in the field of view, a pupil illuminating system for illuminating the pupil of the eye, an imaging optical system for projecting an image of the pupil illuminated by the pupil illuminating system, and an image of the cornea of the eye, composed of light reflected by the cornea, onto an imaging surface, a light-beam-presenting system for preliminarily presenting the stimulating light beams to the eye while moving the stimulating light beams to a particular point in the field of view of the eye, and a computer unit for calculating the direction of the line of sight of the eye. The computer unit controls the light-beam-presenting system to preliminarily present the stimulating light beams to the eye while moving the stimulating light beams to the particular point. The computer unit also calculates the value of parameters relating to the image of the pupil and the image of the cornea, composed of light reflected by the cornea, which vary for different individuals, using the positional relationship between the image of the pupil and the image of the cornea, composed of light reflected by the cornea, when the eye views the preliminarily presented stimulating light beams. The computer unit also calculates the direction of the line of sight of the eye during the measurement of the field of view by the field-of-view measuring system. The perimeter can further comprise a fundus photographing device for photographing a fundus.

According to still another aspect, the present invention which achieves these objectives relates to a focus apparatus comprising a first projection unit for projecting an image of an object, a monitor unit for displaying the image of the object at a particular point to present the image of the object at the particular point to an eye of an observer, and a photoelectric detector for projecting an image of the eye onto the photoelectric detector. The image of the cornea of the eye, composed of light reflected by the cornea, and an image of the pupil of the eye are projected by the second projection unit onto the photoelectric detector and are detectable by the photoelectric detector. The apparatus further comprises a calculation unit for calculating the direction of the line of sight of the eye while the eye observes the image of the object on the monitor unit from the positional relationship between the image of the cornea, composed of light reflected by the cornea, and the image of the pupil detected by the photoelectric detector. The calcuation unit calculates the direction of the line of sight using parameters relating to the image of the pupil and the image of the cornea, composed of light reflected by the cornea, the values of which vary for different observers. The calculation unit also obtains the values of the parameters from the positional relationship between the image of the pupil and the image of the cornea, composed of light reflected by the cornea, on an imaging surface of the photoelectric detector when the eye views the particular point. The apparatus further comprises a focus system for performing a focus operation for focusing the first projection unit according to a focus state of the first projection unit, on a portion of the object corresponding to a portion of the image of the object displayed on the monitor unit presented to the eye in the direction of the line of sight of the observer calculated by the calculation unit.

According to still another aspect, the present invention which achieves these objectives relates to a method of detecting the direction of the line of sight of the eye of an individual. The method comprises the steps of imaging an image of the pupil of the eye and an image of the cornea of the eye, composed of light reflected by the eye, on an imaging surface, preliminarily presenting an image at a particular point to the eye, calculating the values of parameters relating to the image of the pupil and the image of the cornea, composed of light reflected by the cornea, which vary for different individuals, the values of the parameters being obtained by the positional relationship between the image of the pupil and the image of the cornea, composed of light reflected by the cornea, when the eye views the image at a particular point, and calculating the direction of the line of sight of the eye. The direction-of-line-of-sight calculating step is performed using the positional relationship between the image of the pupil and the image of the cornea, composed of light reflected by the cornea, on the imaging surface when the direction of the line of sight is to be measured, and using the value of the parameters.

These and other objects, advantages and features of the present invention will become more apparent from the following detailed description of preferred embodiments taken in connection with the accompanying drawings.

BRIEF DESCRIPTION OF THE DRAWINGS

FIGS. 3(a)–3(c) are diagrams illustrating the output values of video signals from an image pickup device of the present invention;

FIG. 4 is a diagram illustrating the positions of the image of the pupil of an eye and the image of light reflected by the cornea of the eye;

DESCRIPTION OF THE PREFERRED EMBODIMENTS

Each of the following apparatuses for detecting the direction of the line of sight of an eye according to embodiments of the present invention includes pupil illuminating means for illuminating the pupil of the eye, imaging means for producing or obtaining an image of the pupil illuminated by the pupil illuminating means and an image of the cornea of the eye composed of light reflected by the cornea, presenting means for preliminarily presenting an image positioned at a particular point to the eye to be tested, and a direction-of-line-of-sight calculating means for calculating the direction of the line of sight of the eye while the line of sight is measured using the positional relationship between the image of the pupil and the image of the cornea composed of light reflected by the cornea on the imaging means when the eye views the image at the preliminarily presented particular point.

The apparatus for detecting the direction of the line of sight of an eye having the above-described configuration preliminarily presents the image at the particular point to the eye using the presenting means, and detects the subsequent direction of the line of sight of the eye using the positional relationship between the image of the pupil and the image of the cornea composed of light reflected by the cornea on the imaging means when the eye views the image at the particular point.

A first embodiment of the present invention will now be explained in detail.

Figure 1:
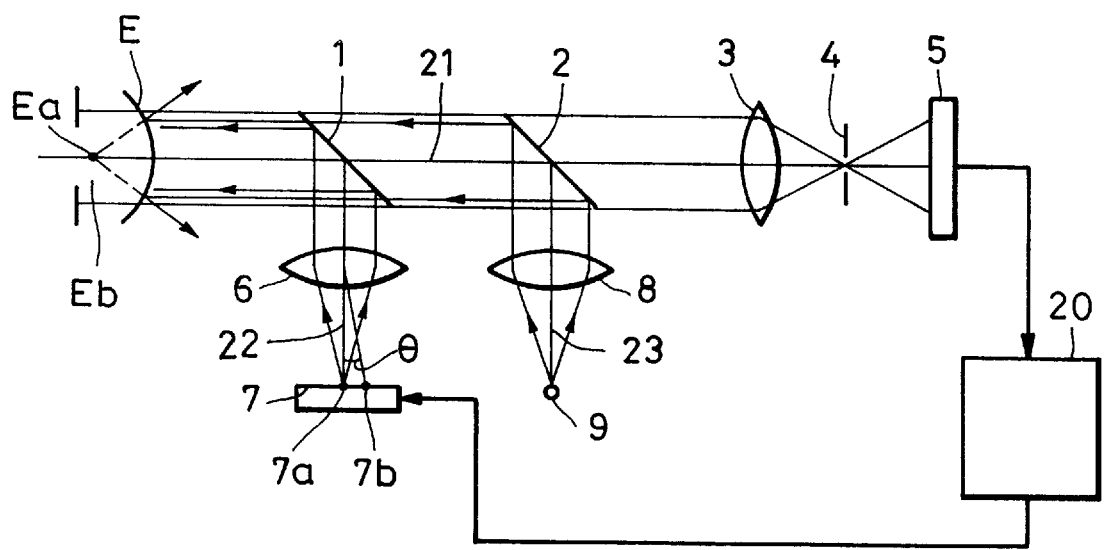
FIG. 1 is a schematic diagram showing the configuration of a first embodiment of the present invention.

FIG. 1 is a diagram showing the configuration of the first embodiment. A dichroic mirror 1 for reflecting visible light beams and transmitting near-infrared light beams, a half-mirror 2, a lens 3, a diaphragm 4 and an image pickup device 5 are sequentially arranged on an optical axis 21, with mirror 1 closest to an eye E to be tested and device 5 furthest from the eye E, for measuring the eye's line of sight. A lens 6, an observation surface 7, such as the focusing glass of an optical finder, the monitoring surface of a video camera, or the like, are provided on an optical axis 22 in the direction of reflection of the dichroic mirror 1. A lens 8 and a light source 9, for detecting the line of sight, which emits infrared light beams, are arranged on an optical axis 23 in the direction of reflection of the half-mirror 2. There is also shown a calculation unit 20, such as a microcomputer or the like.

Visible light beams from the observation surface 7 pass through the lens 6 and reach the eye E by being reflected by the dichroic mirror 1. A person to be tested watches the observation surface 7. While the person watches an image on the observation surface 7, the direction of the line of sight of the eye E is always detected in the following manner. That is, the infrared light beams from the light source 9 for detecting the line of sight are made to be parallel light beams by the lens 8. The parallel light beams are reflected by the half-mirror 2, and are incident upon the eye E by passing through the dichroic mirror 1. The light beams reflected by the pupil and the cornea of the eye E return along the same optical path, are transmitted through the half-mirror 2, and are imaged onto the image pickup device 5 via the lens 3 and the diaphragm 4.

The positions Ea and Eb of the images of the cornea (the images being composed of light reflected by the cornea) when the eye E watches point 7a on the optical axis of the observation surface 7 and when the eye E watches point 7b at an angle of inclination θ with respect to the optical axis 22, that is, when the line of sight has the angle of inclination θ with respect to the measuring optical axis 21 are different. Accordingly, the positions of the images of the cornea observed on the image pickup device 5 are also different. Hence, the angle of inclination θ is detected from the positions of the images of the cornea from light reflected by the cornea in the following manner.

Figure 2:
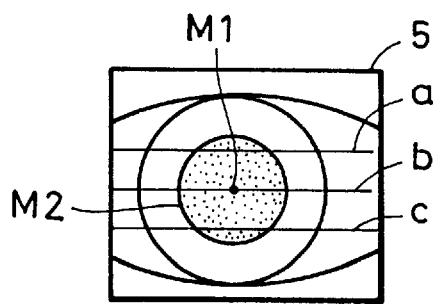
FIG. 2 is a diagram illustrating an image of light received by an image pickup device.

FIG. 2 shows images observed on the image pickup device 5. If video signal outputs on three scanning lines a, b and c on the image pickup device 5 are used, as shown in FIGS. 3(a)–3(c), the video signal output values can be distinctly discriminated at the portion of the image M1 of the cornea composed of light reflected by the cornea and at the portion of the image M2 of the pupil. Hence, by setting an appropriate threshold value, the center of the image M2 of the pupil and the position of the image M1 of the cornea composed of light reflected by the cornea can be easily detected.

FIG. 4 is a diagram illustrating the positional relationship between the image M1 of the cornea composed of light reflected by the cornea and the image M2 of the pupil when the direction of the line of sight of the eye E has an angle of inclination θ with respect to the optical axis 21 for measuring the line of sight. When measuring light beams are incident with the angle of inclination θ with respect to the direction of the line of sight of the eye E, that is, ocular axis 24, the light beams are reflected in the direction of optical axis 25 having an angle of inclination 2θ with respect to the optical axis 01 for measuring the line of sight at the apex P1 of the cornea of the eye E, and are received by the image pickup device 5. Accordingly, if a point separated from the apex P1 of the cornea by r/2 on the ocular axis 24 is represented by P2, where r is the radius of curvature of the cornea, the position of the image M1 of the cornea composed of light reflected by the cornea, on the image pickup device 5 is point P3 on the optical axis 25. If the apparent position of the pupil is assumed to be the center Q1 of the broken line Q shown in FIG. 4, the distance d between the position P3 of the image M1 of the cornea seen from the direction of observation, that is, obtained on the image pickup device 5, and the center Q1 of the pupil in a direction orthogonal to the optical axis 21 is expressed by the following expression, using the angle of inclination θ, the radius r of curvature of the cornea, and the distance L between the points P2 and Q1:

$$\begin{aligned} d &= (r/2) \cdot (\sin 2\theta/\cos\theta) - L\sin\theta \quad (1) \\ &= (r-L)\sin\theta, \end{aligned}$$

since sin 2θ=2 sinθ·cosθ.

In general, since individuals differ in the radius r of the curvature of the cornea, and the distance L of the eye E, it is impossible to obtain the relationship between the distance d and the angle of inclination θ from expression (1) unless the values r and L are detected for each person tested. However, if the value of the distance d can be detected at one value of the angle of inclination θ, the value of parameter (r−L), which is peculiar to an eye of each person, can be obtained. Suppose that a point on the observation surface 7 seen by the person to be tested when the line of sight of the person makes an angle θ1 (≠0) with respect to the optical axis 21 is represented by 7b1. The angle of the line of sight with respect to the optical axis 21 is adjusted to the angle θ1 by making the person watch the point 7b1 by, for example, lighting the point 7b1 on the observation surface 7 according to a command of the calculation unit 20. The distance d1 between the image M1 of light reflected by the cornea and the center Q1 of the pupil is obtained from the output of the image pickup device 5 by the calculation unit 20. Data of the angle θ1 corresponding to the point 7b1 are stored in the calculation unit 20. The value of parameter (r−L) can be obtained by substituting the values d1 and θ1 into expression (1). The calculation unit 20 stores the value.

If the value of parameter (r−L) is obtained and substituted into expression (1), the angle of inclination θ can be thereafter obtained for an arbitrary value of the distance d from expression (1). That is, the calculation unit 20 exactly calculates the value of the angle θ of the line of sight only by measuring the value d in the subsequent measurement. Since the imaging optical system of the present embodiment is a telecentric optical system in which the diaphragm 4 is disposed at the rear-side focus position of the lens 3, the magnification of the image on the image pickup device 5 does not change even if the eye E moves in a direction along the optical axis 21.

In the above-described explanation, it is assumed that the axis of the ocular optical system substantially coincides with the line of sight of the eye. That is, if θ=0 in expression (1), d=0. Actually, the image of the cornea composed of light reflected by the cornea in general deviates from the center of the pupil even when θ=0. In such a case, the values d and θ are decomposed into components in the direction of the deviation and a direction perpendicular thereto. That is, the distance dx in the direction of the deviation and the distance dy in a direction perpendicular thereto between the image of the cornea composed of light reflected by the cornea and the center of the image of the pupil are detected, and the detected values are substituted into expression (1) to obtain the components θx and θy in the respective directions of the angle of inclination θ of the line of sight with respect to the optical system. The value dx corresponding to the distance d0 when θ=0 is obtained from the output of the image pickup device 5. The distance between the image of the cornea and the center of the image of the pupil obtained by lighting point 7a on the observation surface and making the person watch the point 7a is obtained and stored as the value d0.

Figure 5:
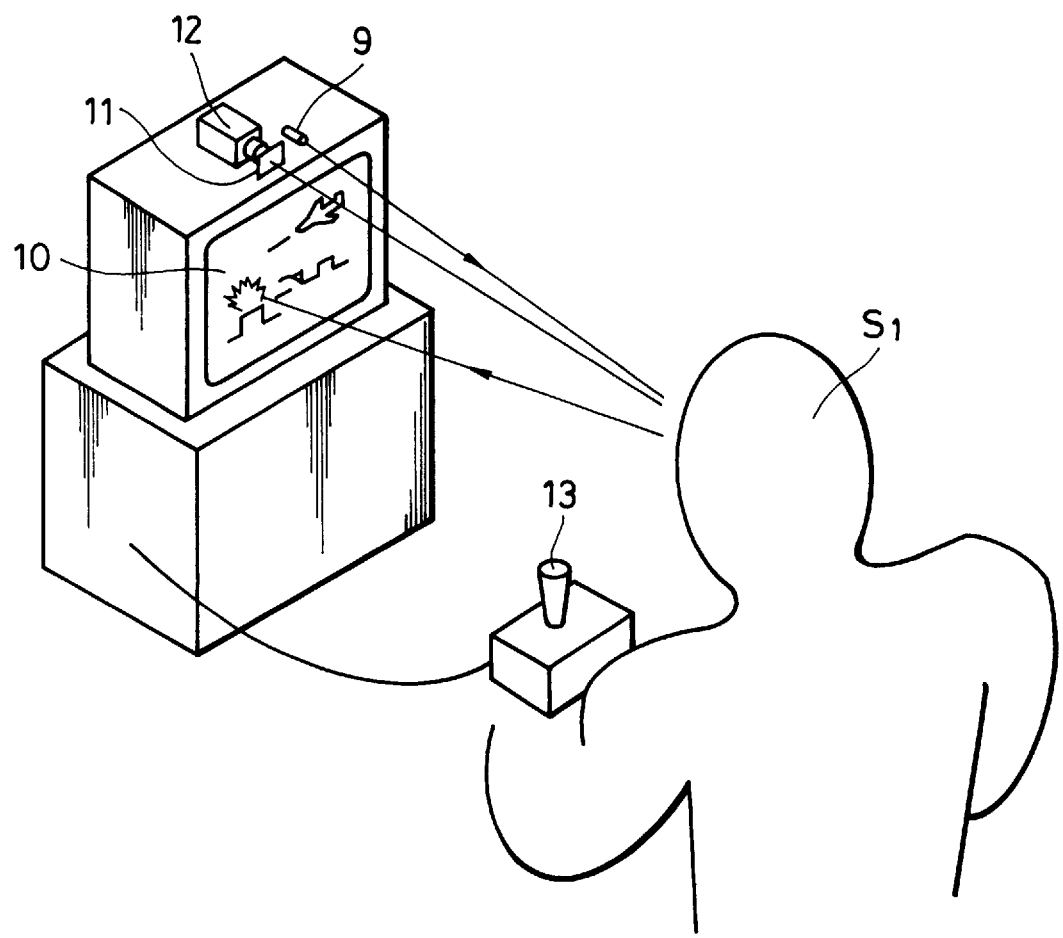
FIG. 5 is a perspective view showing the configuration of a second embodiment of the present invention.

FIG. 5 is a diagram of the configuration of a second embodiment of the present invention in which the invention is applied to a television game machine. A television camera 12 provided with a cold mirror 11 having an optical axis common to that of the television camera 12 in front thereof. The camera 12 and the mirror 11 are mounted on a portion above a cathode ray tube picture surface 10 disposed facing an operator S1. A light source 9 for detecting the line of sight is disposed to one side of the television camera 12. The light source 9 for detecting the line of sight of an eye, the CRT picture surface 10 and the television camera 12 are connected to a microcomputer (not shown) provided behind the CRT picture surface 10. The microcomputer is also connected to a manipulator 13 so that the operator S1 can operate the manipulator 13. As in the first embodiment, the light source 9 and television camera 12 may be arranged on an optical system whose optical axis coincides with that of these units.

The operation of this apparatus will now be described.

First, the operator S1 adjusts the directions in which the light source 9 and the television camera 12 point so that his own eye is imaged on the cold mirror 11 mounted in front of the television camera 12. Subsequently, a viewing target for calibration is sequentially presented at one point on the CRT picture surface 10, infrared light beams are emitted from the light source 9, for detecting the line of sight, toward the eye of the operator S1, light beams reflected by the pupil and the cornea of the eye of the operator S1 are received by the television camera 12, and the proportional coefficient (r−L) between the distance d and the angle of inclination θ is calculated in the same manner as in the first embodiment. At that time, it is assumed that the relationship between the position of the viewing target and the angle of the line of sight with respect to the optical axis of the television camera 12 is previously obtained and is stored in the microcomputer. It is convenient for the operator S1 to perform the positioning of the viewing target for calibration and the like by the operation of the manipulator 13. A game using the television can be performed by a change in the direction of the line of sight of the operator S1 and the operation of the manipulator 13.

Although, in the present embodiment, the apparatus for detecting the line of sight is applied to a television game machine, the present invention may also be applied to various kinds of control devices, such as video cameras and the like, which utilize the direction of the line of sight as the input.

As explained above, since the apparatuses for detecting the direction of the line of sight of an eye according to the present embodiment detect the direction of the line of sight after performing preliminary measurement from the image of the cornea of the eye using light reflected by the cornea and the image of the pupil of the eye, individual differences in r and L are irrelevant, and high accuracy in measurement is obtained.

Each of the following perimeters according to another embodiment of the present invention, for measuring the field of view of an eye of an individual to be tested by presenting an image positioned at a particular point in the field of view of the eye, and obtaining information on when the image is in the field of view of the eye by questioning the individual while the position of the particular point is moved includes a pupil illuminating means for illuminating the pupil of an eye of an individual, imaging means for obtaining an image of the pupil of the eye illuminated by the pupil illuminating means and an image of the cornea of the eye using light reflected by the cornea, and a direction-of-line-of-sight calculating means for preliminarily presenting an image positioned at the particular point to the eye and calculating the direction of the line of sight of the eye while the field of view is measured using the positional relationship between the image of the pupil and the image of the cornea composed of light reflected by the cornea when the eye views the presented image at the particular point.

The perimeter having the above-described configuration preliminarily presents an image at the particular point to the eye, and calculates the direction of the line of sight of the eye while the field of view of the eye is measured using the positional relationship between the image of the pupil and the image of the cornea composed of light reflected by the cornea when the eye views the preliminarily presented image at the particular point.

The embodiments will now be explained in detail with reference to the drawings.

Figure 6:
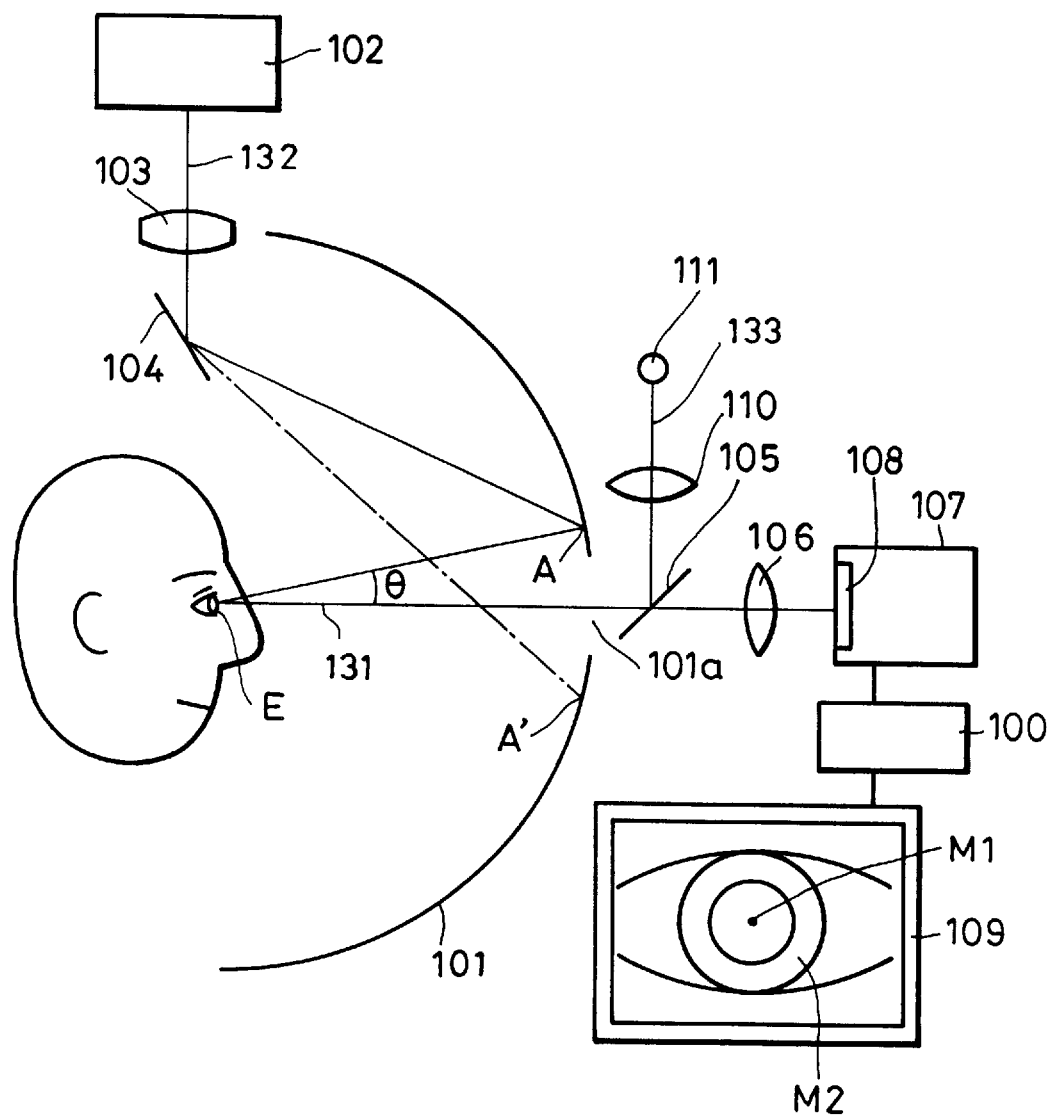
FIG. 6 is a schematic diagram showing the configuration of a third embodiment of the present invention.

FIG. 6 is a diagram showing the configuration of a third embodiment of the present invention. In FIG. 6, a semi-spherical screen 101 having a small opening 101a on an optical axis 131 for measuring the line of sight is provided facing an eye E to be tested. A stimulating light generating apparatus 102 for emitting visible light beams, and a lens 103 are provided outside the screen 101. By changing the angle of a mirror 104 with respect to the optical axis 132 of the stimulating light generating apparatus 102, stimulating light can be guided to an arbitrary position on the inner side of the screen 101 to be presented to the eye E as an image. Although a fixed viewing target (not shown) is provided in the direction of the optical axis 131, the small opening 101a may be used in place of the fixed viewing target. A half-mirror 105, a lens 106, and an image pickup device 108 of a television camera 107 are arranged on the optical axis 131 behind the small opening 101a. The output of the television camera 107 is connected to a television monitor 109 via a microcomputer 100. A lens 110 and an infrared-light-beam light source 111 are sequentially disposed on an optical axis 133 in the direction of reflection of the half-mirror 105.

During measurement of the field of view of the eye E, visible light beams for measuring the field of view are emitted from the stimulating light generating apparatus 102. The emitted light beams proceed on the optical axis 132, are reflected by the mirror 104 via the lens 103, and are presented, for example, at point A or at point A' on the screen 101 as a spot image. By moving the position of the stimulating point by tilting the mirror 104, the tester performs measurement of the field of view while asking the person to be tested if he can see the point.

In the present embodiment, the angle of inclination θ of the direction of the line of sight of the eye E with respect to the optical axis 131 during measurement of the field of view is always measured in the following manner. Hence, it is possible to detect the angle between the direction of the line of sight and the direction of presentation of the stimulating light for measuring the field of view, and to calculate information on measurement of the corrected field of view using the information of the angle. Correction is performed, for example, by subtracting a variance of the direction of the line of sight calculated during measurement from the measured field of view.

A method of detecting the angle of inclination θ will now be explained. During measurement of the field of view, when the infrared-light-beam light source 111 for detecting line of sight is lit, the light beams proceed along the optical axis 133, are made to be parallel light beams via the lens 110, are then reflected by the half-mirror 105, and reach the eye E. The light beams reflected by the cornea of the eye E are imaged onto the image pickup device 108 by the lens 106 together with the light beams reflected by a front portion of the eye E, and the image M1 of the cornea composed of light reflected by the cornea and the image M2 of the front portion of the eye E are presented on the television monitor 109 as shown in FIG. 6. Since the light beams from the infrared-light-beam light source 111 are made to be parallel light beams by the lens 110 and are projected onto the eye E, the positional relationship between the center of the pupil and the image of the cornea composed of light reflected by the cornea will not change even if the eye E moves within a plane perpendicular to the optical axis 131.

Figure 7:
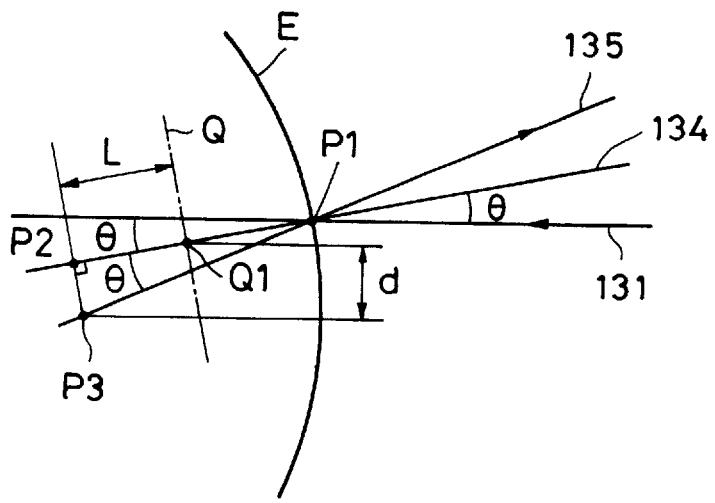
FIG. 7 is a diagram illustrating the positions of the image of the pupil of an eye and the image of light reflected by the cornea of the eye.

FIG. 7 is a diagram illustrating the positional relationship between the image M1 of light reflected by the cornea and the image Ep of the pupil when the direction of the line of sight of the eye E makes an angle of inclination θ with respect to the optical axis 131 for measuring the line of sight. When measuring light beams are incident at an angle of inclination θ with respect to the direction of the line of sight of the eye E, that is, the ocular axis 134, the light beams are reflected in the direction of optical axis 135 having an angle of inclination 2θ with respect to the optical axis 131 for measuring the line of sight at the apex P1 of the cornea of the eye E, and are received by the image pickup device 108. Accordingly, if a point separated from the apex P1 of the cornea by r/2 on the ocular axis 134 is represented by P2, where r is the radius of curvature of the cornea, the position of the image M1 of the cornea composed of light reflected by the cornea on the television monitor 109 is point P3 on the optical axis 135. If the apparent position of the pupil is assumed to be the center Q1 of the broken line shown in FIG. 7, the distance d between the position P3 of the image M1 of light reflected by the cornea seen from the direction of observation, that is, observed on the television monitor 109, and the center Q1 of the pupil in a direction orthogonal to the optical axis 131 is expressed by the following expression using the angle of inclination θ, the radius r of curvature of the cornea, and the distance L between the points P2 and Q1:

$$\begin{aligned} d &= (r/2) \cdot (\sin 2\theta/\cos\theta) - L\sin\theta \\ &= (r-L)\sin\theta. \end{aligned}$$

This is equal to the above-described expression (1).

In general, since individuals differ in the radius r of the curvature of the cornea, and the distance L of the eye E, it is impossible to obtain the relationship between the distance d and the angle of inclination θ from expression (1) unless the values r and L are detected for each person tested. However, as described above, if the value of the distance d can be detected at one value of the angle of inclination θ, the value of parameter (r–L) can be obtained. If the value of parameter (r–L) is obtained, the angle of inclination θ can be obtained for an arbitrary distance d. More specifically, stimulating light beams are projected in a direction other than the optical axis 131, such as point A (the angle of inclination θ of the direction of the line of sight when this point is seen is known), the distance d is measured while the person to be tested watches in the direction, and the proportional coefficient (parameter (r–L)) is calculated by substituting the obtained value d and the value θ at that time into expression (1).

Subsequently, the angle of inclination θ of the line of sight is obtained from the value d obtained from the image pickup device 108 using expression (1) into which the obtained value (r–L) is substituted.

The above-described calculation of the value (r–L), the calculation of the angle of inclination θ, and driving control of the mirror 104 are performed by the microcomputer 100.

The movement of the position of presentation of the stimulating light beams during measurement of the field of view may be performed by a preset program. Alternatively, the next position of presentation of the stimulating light beams may be determined by adding the detected angle of inclination θ for each presentation of the light beams assuming that the direction of the line of sight changes very little between the preceding presentation and the present presentation. If the fact that the distance does not become d=0 when θ=0 causes a problem, the value $d_0$ may be obtained, and the value $d_x$ of deviation from the value $d_0$ in the direction of the deviation may be substituted into expression (1) as the value d in the same manner as in the first embodiment.

Figure 8:
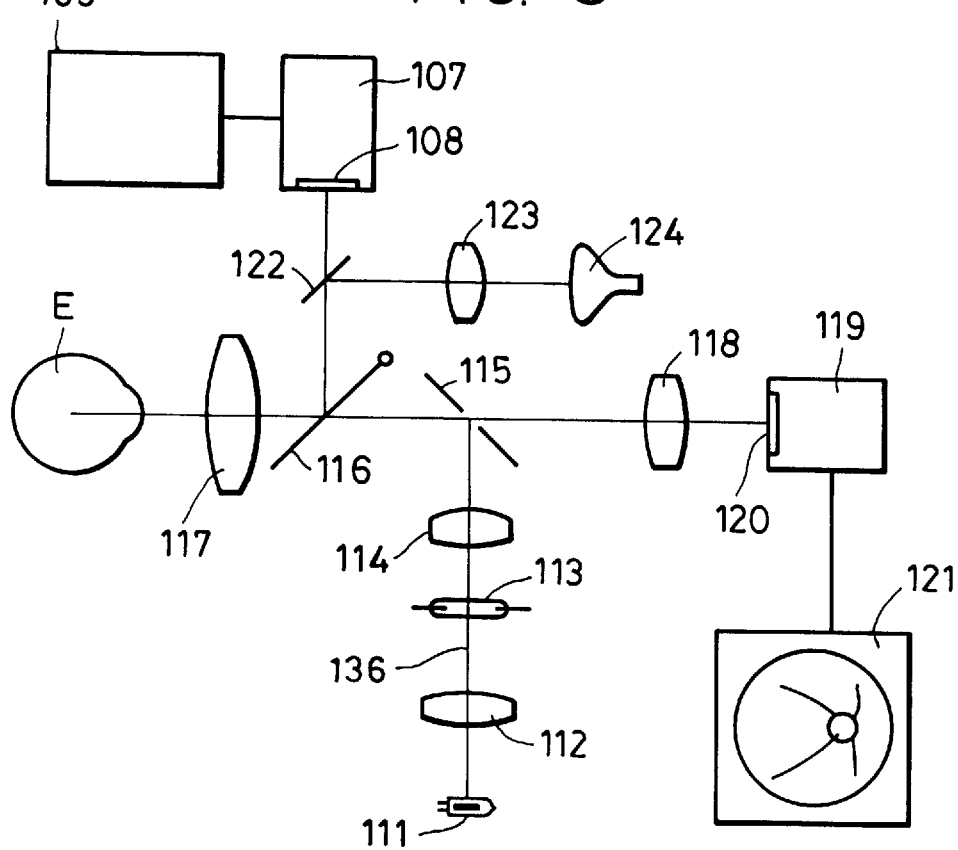
FIG. 8 is a schematic diagram showing the configuration of a fourth embodiment of the present invention.

FIG. 8 is a diagram showing the configuration of a fourth embodiment of the present invention in which the invention is applied to a fundus perimeter. Reference numerals shown in FIG. 8 that are the same as reference numerals used in FIG. 6 denote the same or similar elements. In FIG. 8, on an optical axis 136 from an infrared light source 111 for observing a fundus and detecting the line of sight to an eye E to be tested, a lens 112, a stroboscopic light source 113 for photographing a fundus which emits visible light beams, a lens 114, a perforated mirror 115, a lift mirror 116 insertable in the optical axis 136 for totally reflecting visible light beams and half reflecting infrared light beams, and an objective lens 117 are sequentially arranged. A lens 118 and an image pickup device 120 of a television camera 119 are arranged behind the perforated mirror 115. The output of the television camera 119 is connected to a television monitor 121.

A half-mirror 122 for reflecting visible light beams and transmitting infrared light beams is disposed in the reflecting direction of the lift mirror 116. An image pickup device 108 of a television camera 107 is disposed in the transmitting direction of the half-mirror 122, and a lens 123 and a cathode ray tube 124 for displaying background light, stimulating light and a fixed lamp are disposed in the reflecting direction of the half-mirror 122. Since the perforated mirror 115 is conjugate with respect to a front portion of the eye E with respect to the objective lens 117, the light beams reflected by the cornea of the eye are not included in the image of the fundus imaged by the image pickup device 120.

In measurement of the field of view, if the fixed lamp and the stimulating light are displayed on the CRT 124 in a state of inserting the lift mirror 116 on the optical axis 136, visible light beams from the CRT 124 pass through the lens 123, are reflected by the half-mirror 122 and the lift mirror 116, and reach the eye E via the objective lens 117. Measurement of the field of view of a person to be tested is performed by making him fixedly watch the fixed lamp and tell whether or not he can see the stimulating light displayed around the fixed lamp.

During this measurement of the field of view, the infrared light source 111 is lit in order to measure the angle of inclination θ between the direction of the fixed lamp and the direction of the line of sight of the eye E. Infrared light beams from the infrared light source 111 proceed along the optical axis 136, pass through the lens 112, the stroboscopic light source 113 for photographing a fundus, and the lens 114, are reflected by the perforated mirror 115, and reach the eye E via the lift mirror 116 and the objective lens 117. The light forming the image of the cornea of the eye E and the image of the pupil of the eye E return along the same optical path, are reflected by the lift mirror 116, are imaged on the image pickup device 108 via the half-mirror 122, and are displayed on a television monitor 109. The angle of inclination θ of the line of sight is calculated from the distance d between the center Q1 of the pupil and the image of the cornea, as in the third embodiment.

Infrared light beams reflected by the fundus of the eye E pass through the lift mirror 116, the opening of the perforated mirror 115, and the lens 118, are then imaged on the image pickup device 120 of the television camera 119, and are displayed on the television monitor 121. The tester observes the displayed image. In photographing the fundus, the lift mirror 116 is retracted from the optical axis 136, and the stroboscopic light source 113 for photographing a fundus is lit. The light beams from the stroboscopic light source 113 pass along the same optical path as the light beams for observing the fundus, and reach the eye E, whereby a clear image of the fundus is imaged on the image pickup device 120.

In the perimeters of the above-described embodiments, since the direction of the line of sight of the eye during measurement of the field of view of the eye is calculated, the information on measurement of the corrected field of view can be calculated. Hence, the eye to be tested need not continue to fixedly watch the fixed lamp during measurement of the field of view, and accuracy in the measurement of the field of view is increased. In addition, the measuring time is reduced, and the burden on the person to be tested is also reduced.

Each of the following focus apparatuses according to still another embodiment of the present invention includes projection means for projecting the image of an object, display means for displaying the image of the object at a particular point to present the image of the object at the particular point to an eye of an observer, illumination means for illuminating the eye of the observer observing the display means with light beams, projection means for projecting the image of the eye of the observer onto a photoelectric detector, line-of-sight detection means for detecting light reflected by the cornea of the eye forming an image of the cornea of the eye and an image of the pupil of the eye from an output of the photoelectric detector and obtaining the direction of the line of sight from the positional relationship between the two images, and focus means for performing a focus operation, using a signal of a photographing means, on a portion of the object corresponding to of a portion of the image of the object displayed on the display means presented to the eye in the directon of the line of sight obtained by the line-of-sight detection means.

The focus apparatus having the above-described configuration illuminates the eye of the observer with light beams, photoelectrically detects the positions of the image of the cornea of the eye composed of light reflected by the cornea and the image of the pupil of the eye, detects the direction of the line of sight of the eye from the positional relationship between the two images, and performs a focusing operation on a portion of the object corresponding to a portion of the image of the object displayed on the display means presented to the eye in the direction of the line of sight.

The embodiments will now be explained in detail with reference to the drawings.

Figure 9:
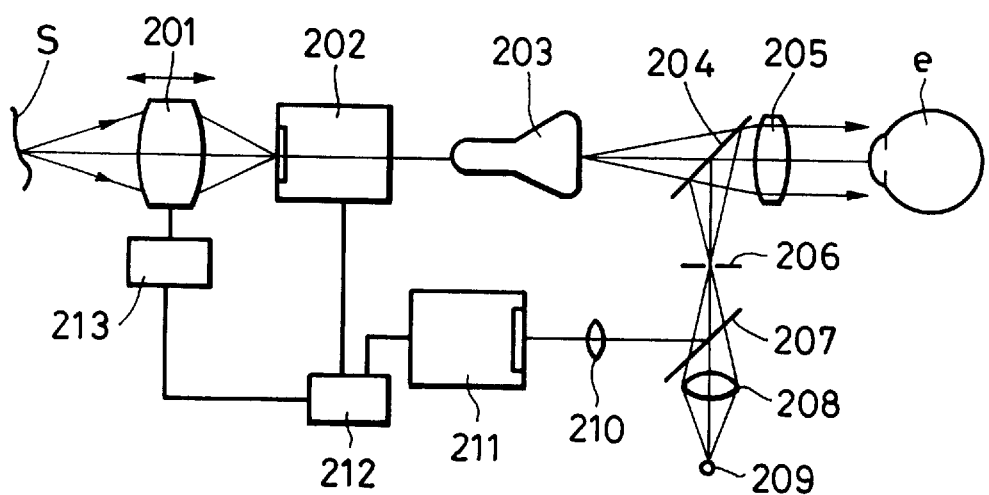
FIG. 9 is a schematic diagram showing the configuration of a fifth embodiment of the present invention.

FIG. 9 shows a fifth embodiment of the present invention in which the invention is applied to a video camera. In FIG. 9, a first imaging means 202 is disposed in front of a lens 201 facing an object S. The output of the imaging means 202 is connected to a cathode ray tube 203. A dichroic mirror 204 and a magnifying lens 205 are arranged on an optical path in front of the CRT 203 so that an eye e of an observer can observe an image on the CRT 203 via the magnifying lens 205. A diaphragm 206, a light dividing member 207 comprising a half-mirror, a lens 208 and a light source 209 comprising an LED (light-emitting diode) for emitting near-infrared rays are sequentially arranged in the direction of reflection of the dichroic mirror 204. A lens 210 and a second imaging means 211 are arranged in the direction of reflection of the light dividing member 207. The output of the second imaging means 211 is connected to a calculation means 212, which is connected to the first imaging means 202. The output of the calculation means 212 is connected to a lens driving means 213 for driving the lens 201.

The image of the object S imaged by the first imaging means 202 via the lens 201 is displayed on the CRT 203, and reaches the eye e of the observer while being magnified by the magnifying lens 205. Infrared light beams emitted from the light source 209 are made to be parallel light beams after passing through the lens 208, and then pass through the light dividing member 207, the diaphragm 206, the dichroic mirror 204 and the magnifying lens 205, and enter the eye e, and are reflected by the cornea of the eye e. The light reflected by the cornea and the image of a front portion of the eye e are imaged onto the second imaging means 211 via the magnifying lens 205, the dichroic mirror 204, the light dividing member 207 and the lens 210.

Figure 10A:
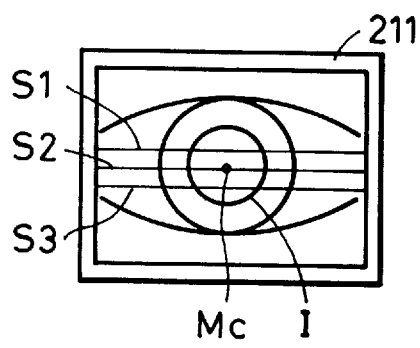
FIGS. 10(a) and 10(b) are diagrams illustrating the images of light reflected by the cornea of an eye and the image of a front portion of the eye.
Figure 10B:
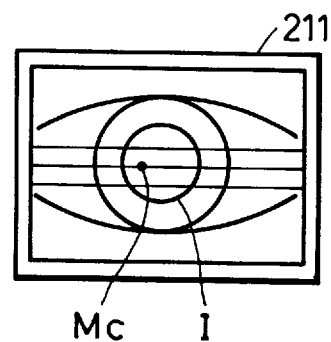

FIGS. 10(a) and 10(b) show images obtained by the second imaging means 211. FIG. 10(a) shows the case in which the eye e is directed in the direction of the optical axis. In FIG. 10(a), the image Mc of the cornea composed of light reflected by the cornea appears in the center of the pupil I. FIG. 10(b) shows the case in which the eye e is directed in an oblique direction. In FIG. 10(b), the image Mc of the cornea composed of light reflected by the cornea appears eccentric relative to the pupil I, i.e., shifted away from the center of the pupil I.

As described above, the amount of eccentricity d is expressed by the following expression from the geometrical relationship:

$$d = (1/2) \cdot (r\sin 2\theta/\cos\theta) - L\sin\theta \quad (1)$$
$$= (r - L)\sin\theta,$$

where r represents the radius of curvature of the cornea, L represents the apparent depth of the pupil from the apex of the cornea, and $\theta$ represents the direction of the line of sight of the eye with respect to the optical axis. As described above, if the fact that the value d is not d=0 when $\theta$=0 causes a problem, the value $d_0$ may be obtained, and the value $d_x$ of deviation from the value $d_0$ in the direction of the deviation may be substituted into expression (1) as the value d.

For obtaining the angle of eccentricity $\theta$ and the amount d of eccentricity from the image of the front portion of the eye e obtained by the second imaging means 211, the image Mc of the cornea can be detected as a point having the highest luminance in the video signal. Accordingly, as shown in FIGS. 10(a) and 10(b), a scanning line S1 passing this point is chosen, and scanning lines S2 and S3 spaced an equal distance from scanning line S1 are also chosen above and below the scanning line S1. The distribution of luminance on the scanning lines S1, S2 and S3 depends on the eccentricity in accordance with the difference in luminance in an iris portion and a pupil portion. Hence, by performing computer processing of the distributions of luminance, the direction of eccentricity $\theta$ and the amount d of eccentricity are obtained.

Figure 11:
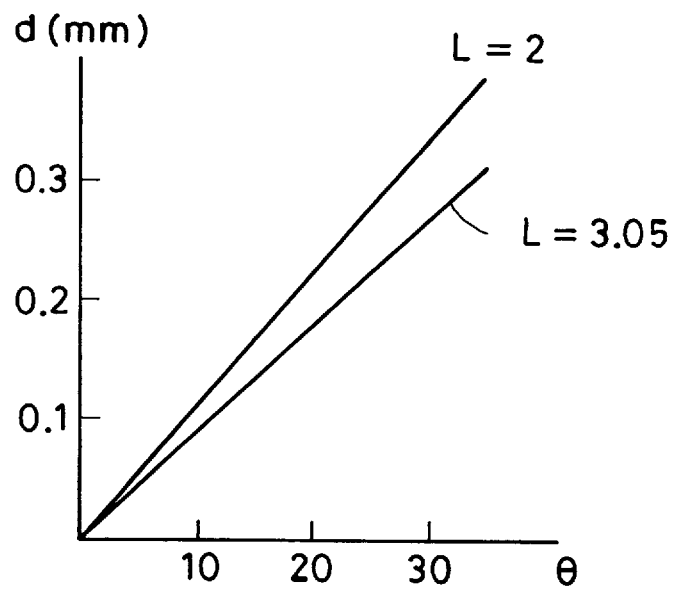
FIG. 11 is a graph showing the relationship between eccentricity d and the direction θ of the line of sight of an eye.

FIG. 11 shows the relationship between the direction $\theta$ and the amount d of eccentricity. Individuals differ in the values of the radius r of curvature of the cornea and the apparent depth L of the pupil. If such individual differences cause a problem, by previously measuring the values of the amount $d_1$ of eccentricity for known values of the angle $\theta$ for each person as described above, the parameter (r–L) can be determined from expression (1), and the relationship between the angle $\theta$ and the amount d can be exactly obtained from expression (1) into which the value of parameter (r–L) has been substituted. For measuring the amount $d_1$ of eccentricity, an appropriate fixed viewing target (the angle $\theta_1$ of the line of sight of the eye when the target is seen is known) may be displayed on the CRT 203, and the amount d of eccentricity when the target is seen may be checked.

Since the direction of the line of sight (the direction $\theta$ of eccentricity) is obtained from the amount d of eccentricity, the calculation means 212 may perform a focus operation using a well-known automatic focusing method, for example, by extracting the signal of a portion corresponding to the direction of the line of sight from the video signal of the first imaging means 202 using a timing circuit, passing the signal through a differential circuit, and driving the lens 201 in the directions of the arrows by the lens driving means 213 so that the output of the differential circuit is maximized.

Figure 12:
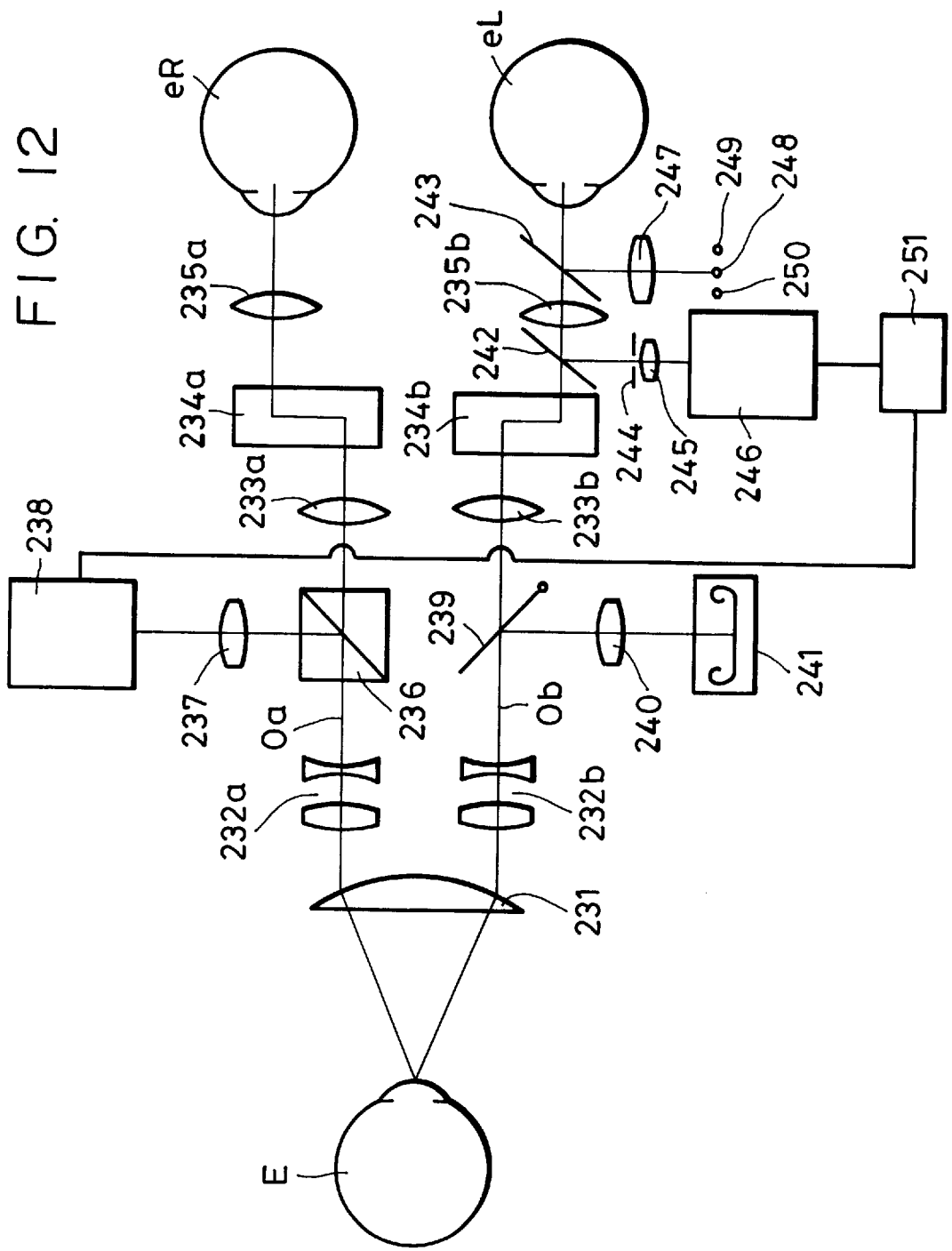
FIG. 12 is a schematic diagram showing the configuration of a sixth embodiment of the present invention.

FIG. 12 is a diagram showing the configuration of a sixth embodiment of the present invention, in which the invention is applied to a slit lamp or an operation microscope used by an oculist. In FIG. 12, the image of an eye E to be tested is guided to an optical path 0a reaching the right eye eR of an observer and an optical path 0b reaching the left eye eL of the observer via a lens 231. Variable-power lenses 232a and 232b, lenses 233a and 233b, erect-image prisms 234a and 234b, and ocular lenses 235a and 235b are sequentially arranged along the optical axes 0a and 0b, respectively. A beam splitter 236 is inserted between the variable-power lens 232a and the lens 233a on the optical axis 0a, and a lens 237 and a third imaging means 238 are arranged at the reflection side of the beam splitter 236.

A lift mirror 239 is inserted between the variable-power lens 232b and the lens 233b in the optical path 0b during a photographing operation, and a lens 240 and a film camera 241 are provided in the direction of reflection of the lift mirror 239. A dichroic mirror 242 and a half-mirror 243 are inserted in front of and behind the ocular lens 235b in the optical path 0b, respectively, and a diaphragm 244, a lens 245 and a fourth imaging means 246 are arranged in the direction of reflection of the dichroic mirror 242. A lens 247, and a light source 248 comprising an LED emitting near-infrared rays are arranged in the direction of reflection of the half-mirror 243. Visible light sources 249 and 250 for correcting the line of sight are provided on both sides of the light source 248 at positions deviated from the optical axis. The outputs of the third and fourth imaging means 238 and 246 are connected to a calculation means 251.

In the above-described configuration, the fourth imaging means 246 images the image of a front portion of the eye eL, and the direction of the line of sight of the eye E is detected in the same manner as in the above-described embodiment. In the present embodiment, however, correction of the direction of the line of sight, that is, determination of parameter (r–L), is performed by lighting any one of the light sources 249 and 250 for correcting the line of sight, and viewing the lit light source with the eye eL of the observer. After detecting the direction $\theta$ of the line of sight, a focus operation may be performed only using the signal of a portion corresponding to the direction $\theta$ of the line of sight in the video signal of the image obtained by the third imaging means 238, as in the above-described embodiment.

In the case of a microscope, focus driving has in general a structure for moving the light sources as one body. In a slit lamp, a focus operation is performed by manually moving a sliding platform back and forth during observation. In an imaging or photographing operation, a focus operation may be performed by driving dedicated lenses, that is, the lenses 237, 232a and 232b.

When accuracy in the direction θ of the line of sight is not required, the visible light sources 249 and 250 are not used. Although it will be convenient for the user to use a two-dimensional image pickup device, such as a CCD (charge-coupled device) or the like, as the imaging means 246, a plurality of one-dimensional devices may also be used. For one-dimensionally detecting a plurality of lines of sight, a one-dimensional CCD will suffice.

As explained above, the focus apparatuses of the above-described embodiments can focus on a desired portion on the picture surface to which the line of sight of an eye of an observer is directed by detecting the direction of the line of sight.

Figure 13:
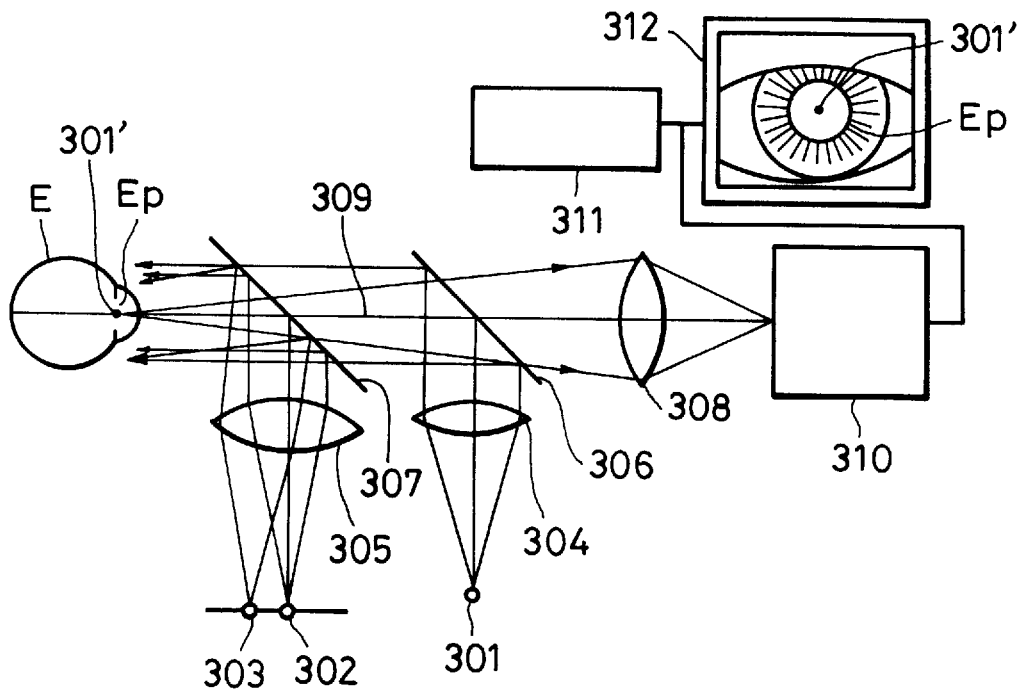
FIG. 13 is a schematic diagram showing the configuration of a seventh embodiment of the present invention.

FIG. 13 shows the configuration of a seventh embodiment of the present invention. In the present embodiment, the invention is applied to a photometer used, for example, for measurement of strabismus, heterophoria and the like. In FIG. 13, near-infrared rays emitted from a light source 301 for measurement are made to be parallel light beams by a lens 304, are reflected by a half-mirror 306, and enter an eye E to be tested after passing through a dichroic mirror 307. The half-mirror 306 has the function of dividing light beams emitted from the light source 301, i.e., reflecting visible light beams and transmitting infrared light beams. Light beams reflected by the eye E pass through the dichroic mirror 307 and the half-mirror 306. A front portion of the eye E is imaged onto the imaging surface of a television camera 310 by a lens 308 constituting an observation optical system. A video signal from the television camera 310 is displayed on a monitor 311, and is also input to a signal processor 312, which calculates the eye position by obtaining the positional relationship between the image of the pupil Ep of the eye E and the image 301' of the cornea of the eye E composed of light reflected by the cornea, as will be described later. Fixed light sources 302 and 303 are provided on the observation surface. The fixed light source 302 is provided on the optical axis of the optical system, and the fixed light source 303 is provided so as to be spaced from the optical axis. Light beams from these fixed light sources are condensed by a lens 305, are reflected by the dichroic mirror 307, and are incident upon the eye E.

Figure 14:
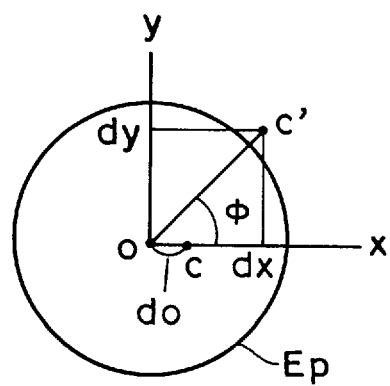
FIG. 14 is a diagram illustrating the positional relationship between respective images.

Next, the principle of photometry will be described in detail. FIG. 14 is a diagram showing the relationship between the position C' of the image of the cornea and the image of pupil Ep on the imaging surface of the television camera 310. Since the optical axis of the eyeball is in general more or less inclined with respect to the direction of the line of sight (the visual line), the image C' of the cornea composed of light reflected by the cornea does not coincide with the center O of the pupil Ep even when the direction of the optical axis 309 of the observing optical system is seen. That is, in general, the light reflected by the cornea shifts toward one side of the nose by a predetermined amount (for example, about 0.4 mm) on the imaging surface. This amount is different for different individuals. The angle made by the line of sight, defined as the line connecting the center of the pupil of the person to be tested and the fixed point which is viewed, and the optical axis of the eyeball, defined as the line connecting the center of the pupil and the center of curvature of the cornea, is called a lambda angle. If the lambda angle is θ, the image of the cornea composed of light reflected by the cornea comes to the center of the image of the pupil on the imaging surface when the person watches the fixed point in the forward direction (the direction of the optical axis of the observation optical system). As described above, the distance d between the image of the cornea composed of light reflected by the cornea and the center of the pupil when the line of sight of the person is in an oblique direction so as to form an angle θ with respect to the optical axis of the observation optical system is represented by $$d=(r-L)\sin\theta \quad (1).$$

If the lambda angle is not 0, that is, if the line of sight is more or less inclined with respect to the optical axis of the eyeball, the distance d between the image of the cornea cpmposed of light reflected by the cornea and the center of the pupil when an oblique direction having an angle θx with respect to the direction connecting the center O of the pupil and the image C' of the cornea composed of light reflected by the cornea (that is, x direction shown in FIG. 14) is seen is expressed by $$d=(r-L)\sin\theta_x + d_0\cos\theta_x \quad (2),$$

where $d_0$ represents the distance between the image of the cornea composed of light reflected by the cornea and the center of the pupil when θx=0, by being influenced by the above-described lambda angle. If it is estimated that the value θx has a value close to 0, the term $d_0\cos\theta_x$ in expression (2) may be replaced by $d_0$.

In general, if the case is considered in which the line of sight is inclined by angles θx and θy in the x and y directions, respectively, with respect to the optical axis 309, the distances dx and dy between the image of the cornea composed of light reflected by the cornea along the x and y directions, respectively, the angle θ of the line of sight with respect to the optical axis 309, and the aximuth φ of the line of sight are expressed as follows:

$$d_x = (r - L)\sin\theta_x + d_0\cos\theta_x \quad (2)$$

$$d_y = (r - L)\sin\theta_y \quad (3)$$

$$\theta = \sqrt{\theta_x^2 + \theta_y^2} \quad (4)$$

$$\phi = \tan^{-1}(\theta_y/\theta_x). \quad (5)$$

Next, the method of measurement will be explained. First, by lighting the light source 302 on the observation surface, the eye E is made to view the light source to adjust the line of sight of the eye E to the optical axis 309 of the observation optical system (that is, θx=θy=0). At that time, the value dx obtained from expression (2) by the signal processor 311 corresponds to the value $d_0$ generated by being influenced by the lambda angle. Expression (2) into which this value $d_0$ is substituted will be hereinafter used. Subsequently, the light source 302 is turned off, and the eye E is made to view the light source 303 by lighting it. Angles θx and θy made by the direction of the line of sight and the optical axis 309 of the observation optical system when the light source 303 is viewed have already been obtained and are therefore known values. At that time, the values dx and dy are obtained from the video signal of the television camera 310 by the signal processor 311. The value (r–L) is calculated from the obtained values using expression (2) or (3). Expressions (2) or (3) into which this value (r–L) is substituted will be hereinafter used. Correction of the calculated expressions are terminated by the above-described processing.

Subsequently, the fixed light source for measuring strabismus is alternately presented to a healthy eye and a diseased eye, and the image of the cornea and the image of the pupil of the diseased eye are imaged by the television camera 310. The values $d_x$ and $d_y$ are obtained from the obtained video signal by the signal processor 311, the values $\theta_x$ and $\theta_y$ are obtained from expressions (2) and (3), and the values of $\theta$ and $\phi$ are further obtained by expressions (4) and (5). Strabismus is measured from the difference between the position of the diseased eye when the healthy eye watches the fixed light source, and the position of the diseased eye when the diseased eye watches the fixed light source. The value $\theta$ represents the angle of strabismus (that is, the inclination of the direction of the line of sight), and the value $\phi$ represents the direction of strabismus.

The fixed light source for measuring strabismus may be placed at a remote position outside the apparatus. In measuring strabismus when a near object is watched, the fixed light source is placed at a position near the eye to be tested. If on-line provision of information is not required, a film camera may replace the television camera 310. When two light sources 301 for measurement are provided at positions symmetrical with respect to the optical axis 309 to perform illumination from two oblique directions, the middle point of two images of light reflected by the cornea on the imaging surface which coincides with the above-described position of the image of light reflected by the cornea may be detected, and measurement may be performed using the distance between the middle point and the center of the pupil. Since the above-described expressions (2) and (3) are obtained by a paraxial approach, some error may be produced as the value $\theta$ increases. Accordingly, a more exact value will be obtained by previously obtaining a corrected value when the value $\theta$ increases, and performing measurement in consideration of the corrected value in actual measurement.

The individual components represented by the blocks shown in FIGS. 1, 5, 6, 8, 9, 12 and 13 are well-known in the optical art and their specific construction and operation is not critical to the invention or the best mode for carrying out the invention. Moreover, the steps recited in the specification for carrying out the present invention can be easily programmed into well-known central processing units by person of ordinary skill in the art and since such programming per se is not part of the invention, no further description thereof is deemed necessary.

What is claimed is:

1. An optical apparatus, comprising:

pupil illuminating means for illuminating the pupil of an eye of an individual;

area sensor means for obtaining an image of the pupil illuminated by said pupil illuminating means and a cornea reflection of said pupil illuminating means, said area sensor means obtaining the image via a beam dividing device;

presenting means for preliminarily presenting at least two visual target points positioned at least in two particular directions with respect to the eye via the beam dividing device; and direction-of-line-of-sight calculation means for calculating the direction of the line of sight of the eye, said direction-of-line-of-sight calculation means calculating the direction of the line of sight of the eye using a positional relationship between the image of the pupil and the cornea reflection on an imaging surface of said area sensor means, and calculating the direction of the line of sight using at least one parameter characteristic of the eye relating to the image of the pupil and the cornea reflection;

wherein the value of said at least one parameter is obtained from the positional relationship between the image of the pupil and the cornea reflection on the imaging surface of said area sensor means when the eye views the at least two visual target points positioned in said at least two particular directions.

2. An apparatus according to claim 1, further comprising perimetric means for presenting stimulating light beams at one point in the visual field of the eye, and measuring the visual field by obtaining information from the individual to be tested while moving the position of said stimulating light beams within the visual field, and wherein said direction-of-line-of-sight calculation means calculates the direction of the line of sight of the eye the visual field of which is measured by said perimetric means.

3. An apparatus according to claim 1, further comprising projection means for projecting the image of an object, and display means for displaying the image of the object to present the image of the object to the individual, wherein said projection means comprises automatic focusing means for performing a focus operation according to a focus condition of said projection means, wherein said direction-of-line-of-sight calculation means calculates the direction of the line of sight while the individual observes said display means, and wherein said automatic focusing means performs a focus operation according to a focus condition of said projection means with respect to a portion of the object corresponding to a portion of the image of the object on said display means presented in the calculated direction of the line of sight of the individual.

4. An apparatus according to claim 1, wherein said apparatus obtains information on eye position strabismus or heterophoria of the individual according to a result of the calculation by said direction-of-line-of-sight calculation means.

5. An apparatus according to claim 1, wherein said two-dimensional image sensor means is a video camera.

6. A direction-of-line-of-sight detecting apparatus, comprising:

pupil illuminating means for illuminating the pupil of an eye of an individual;

area sensor means for obtaining an image of the pupil illuminated by said pupil illuminating means and a cornea reflection of said pupil illuminating means, area sensor means obtaining the image via a beam dividing device;

presenting means for preliminarily presenting at least two visual target points positioned in at least two particular directions with respect to the eye via the beam dividing device; and direction-of-line-of-sight calculation means for calculating the direction of the line of sight of the eye, said direction-of-line-of-sight calculation means calculating the direction of the line of sight of the eye using the positional relationship between the image of the pupil and the cornea reflection on an imaging surface of area sensor means, and calculating the direction of the line of sight using at least one parameter characteristic of the eye relating to the image of the pupil and the cornea reflection, wherein the value of said at least one parameter is obtained from the positional relationship between the image of the pupil and the cornea reflection on the imaging surface of said area sensor means when the eye views the at least two visual target points positioned in said at least two particular directions.

7. An apparatus according to claim 6, further comprising a system for playing a television game, and wherein said system for playing a television game operates according to a result of the calculation of said direction-of-line-of-sight calculation means.

8. An apparatus according to claim 6, wherein said two-dimensional image sensor means is a video camera.

9. A perimeter, comprising:
a visual field measuring system for measuring a visual field of an eye of an examinee on the basis of a response of the examinee when a stimulating light beam is presented at various positions in the visual field;
a pupil illuminating system for illuminating the pupil of the eye, said pupil illuminating system having at least one light source;
an imaging optical system for projecting an image of the pupil illuminated by said pupil illuminating system, and a cornea reflection of said light source;
a light-beam-presenting system for preliminarily presenting the stimulating light beam to the eye at least at one particular point in the visual field of the eye, said light-beam-presenting system comprising a light source for emitting a visible light beam, a lens through which the visible light beam passes, and a movable mirror positioned to receive the visible light beam after passing through said lens and to project the visible light beam at an arbitrary point in front of the eye of the examinee; and
a computer unit for calculating the direction of the line of sight of the eye, said computer unit controlling said light-beam-presenting system to preliminarily present the stimulating light beam to the eye at said at least one particular point, calculating a value of at least one parameter characteristic of the eye by using the positional relationship between the image of the pupil and the cornea reflection when the eye views the preliminarily presented stimulating light beam, and calculating the direction of the line of sight of the eye on the basis of the value of said at least one parameter during the measurement of the visual field.

10. A perimeter comprising:
a visual field measuring system for measuring a visual field of an eye of an examinee on the basis of a response of the examinee when a stimulating light beam is presented at various positions in the visual field;
a pupil illuminating system for illuminating the pupil of the eye, said pupil illuminating system having at least one light source;
an imaging optical system for projecting an image of the pupil illuminated by said pupil illuminating system, and a cornea reflection of said light source;
a light-beam-presenting system for preliminarily presenting the stimulating light beam to the eye at least at one particular point in the visual field of the eye;
a computer unit for calculating the direction of the line of sight of the eye, said computer unit controlling said light-beam-presenting system to preliminarily present the stimulating light beam to the eye at said at least one particular point, calculating a value of at least one parameter characteristic of the eye by using the positional relationship between the image of the pupil and the cornea reflection when the eye views the preliminarily presented stimulating light beam, and calculating the direction of the line of sight of the eye on the basis of the value of said at least one parameter during the measurement of the visual field; and
fundus recording device for recording a fundus.

11. A focus apparatus, comprising:
a first imaging unit for imaging an image of an object;
a displaying unit for displaying the image of the object and for presenting at least two visual target points to an eye of an observer;
area sensor means for detecting light;
light source means for illuminating the pupil of the eye;
a second imaging unit for projecting an image of the eye onto said area sensor means, wherein a cornea reflection of said light source means and an image of the pupil of the eye projected by said second imaging unit onto said area sensor means are detectable by said area sensor means;
a calculation unit for calculating the direction of the line of sight of the eye while the observer views the image of the object on said displaying unit from the positional relationship between the cornea reflection and the image of the pupil detected by said area sensor means, said calculation unit calculating the direction of the line of sight using at least one parameter characteristic of the eye and relating to the image of the pupil and the cornea reflection, and obtaining the value of the parameter from the positional relationship between the image of the pupil and the cornea reflection on an imaging surface of said area sensor means when the eye views said at least two visual target points; and
an automatic focusing system, connected to said calculation unit and said first imaging unit, for performing a focus operation for focusing said first imaging unit, according to the direction of the line of sight of the observer calculated by said calculation unit so that the portion of said displaying unit to which the line of sight of the observer is directed is focused.

12. An apparatus according to claim 11, wherein said two-dimensional photoelectric detector means is a two-dimensional charge coupled device.

13. A method of detecting the direction of the line of sight of an eye of an individual, said method comprising the steps of:
illuminating the pupil of an eye of the individual by illuminating means;
imaging an image of the illuminated pupil and a cornea reflection of said illuminating means on an imaging surface of area sensor means, said imaging the image being performed via a beam dividing device;
preliminarily presenting at least two visual target points positioned in at least two particular directions with respect to the eye via the beam dividing device;
calculating a value of at least one parameter characteristic of the eye and relating to the image of the pupil and the cornea reflection, the value of said at least one parameter being obtained by the positional relationship between the image of the pupil and the cornea reflection when the eye views said at least two visual target points; and
calculating the direction of the line of sight of the eye, said direction-of-line-of-sight calculation step being performed by using a positional relationship between the image of the pupil and the cornea reflection on the imaging surface when the direction of the line of sight is to be measured, and using the value of said parameter.

14. An apparatus according to claim 13, wherein said two-dimensional image sensor means is a video camera.

15. An optical apparatus comprising:
an illuminator for illuminating the pupil of an eye of an individual;
a beam dividing device;
an area sensor for obtaining an image of the pupil illuminated by said illuminator and a cornea reflection of said illuminator, wherein said beam dividing device is positioned between said area sensor and the eye;
a presenting system for preliminarily presenting at least two visual target points positioned at least in two particular directions with respect to the eye, wherein said beam dividing device is positioned between said presenting system and the eye; and
a calculation unit for calculating the direction of the line of sight of the eye, said calculation unit calculating the direction of the line of sight of the eye using a positional relationship between the image of the pupil and the cornea reflection on an imaging surface of said area sensor, and calculating the direction of the line of sight using at least one parameter characteristic of the eye relating to the image of the pupil and the cornea reflection,
wherein the value of the at least one parameter is obtained on the basis of the positional relationship between the image of the pupil and the cornea reflection on the imaging surface of said area sensor when the eye views the at least two visual target points positioned in the at least two particular directions.

16. A direction-of-line-of-sight detecting apparatus, comprising:
a illuminator for illuminating the pupil of an eye of an individual;
a beam dividing device;
an area sensor for obtaining an image of the pupil illuminated by said illuminator and a cornea reflection of said illuminator, wherein said beam dividing device is positioned between said area sensor and the eye;
a presenting system for preliminarily presenting at least two visual target points positioned at least in two particular directions with respect to the eye, wherein said beam dividing device is positioned between said presenting system and the eye; and
a calculation unit for calculating the direction of the line of sight of the eye, said calculation unit calculating the direction-of-line-of-sight of the eye using a positional relationship between the image of the pupil and the cornea reflection on an imaging surface of said area sensor, and calculating the direction of the line of sight using at least one parameter characteristic of the eye relating to the image of the pupil and the cornea reflection,
wherein the value of said at least one parameter is obtained on the basis of the positional relationship between the image of the pupil and the cornea reflection on the imaging surface of said area sensor when the eye views the at least two visual target points positioned in the at least in two particular directions.

17. A method of detecting the direction of the line of sight of an eye of an individual, said method comprising the steps of:
illuminating the pupil of an eye of an individual by an illuminator;
reflecting light representing an image of the pupil and the cornea reflection of the illuminator from the eye to a beam-dividing device positioned between the eye and an area sensor,
imaging the image of the pupil illuminated by the illuminator and the cornea reflection of the illuminator having been reflected from the eye to the beam-dividing device on an imaging surface of said area sensor;
passing light from at least two visual target points to the beam-dividing device and then to the eye to preliminarily present the at least two visual target points to the eye, the at least two visual target points being positioned at least in two particular directions with respect to the eye; and
calculating a value of at least one parameter characteristic of the eye relating to the image of the pupil and the cornea reflection, the value of the at least one parameter being obtained on the basis of the positional relationship between the image of the pupil and the cornea reflection when the eye views the at least two visual target points positioned in the at least two particular directions; and
calculating the direction of the line of sight of the eye, said direction-of-line-of-sight calculating step being performed by using a positional relationship between the image of the pupil and the cornea reflection on the imaging surface when the direction of the line of sight is to be measured, and using the value of the parameter.

18. An optical apparatus, comprising:
an image observing system for presenting an image of an object to an eye of an observer by using an observing optical system;
a visual target point presenting unit for presenting at least two visual target points to the eye;
an illuminating unit for illuminating the pupil of the eye;
an area sensor;
an imaging optical system for projecting an image of an anterior part of the eye onto said area sensor, wherein a cornea reflection of said illuminating unit and an image of the anterior part of the eye projected by said imaging optical system onto said area sensor are detectable by said detector unit;
a calculation unit for calculating the direction of the line of sight of the eye while the observer views the image of the object projected by said image observing system from the positional relationship between the cornea reflection and an image of a pupil of the eye detected by said area sensor, said calculation unit calculating the direction of the line of sight using at least one parameter characteristic of the eye and relating to the image of the pupil and the cornea reflection, and obtaining the value of the parameter from the positional relationship between the image of the pupil and the cornea reflection on said area sensor when the eye views said at least two visual target points; and
an automatic focusing system connected to said calculation unit and said image observing system for performing a focus operation for focusing said observing optical system, according to the direction of the line of sight of the observer calculated by said calculation unit, so that a portion of said observing optical system to which the line of sight of the observer is directed is focused.

19. An apparatus according to claim 18, wherein said detector unit has a two-dimensional image sensor.

20. An apparatus according to claim 18, wherein said image observing system has an image sensor for obtaining an image to be observed and a display unit for displaying the image obtained by said image sensor.

21. A focusing apparatus, comprising:

an image pickup element for picking-up an image of an object through an imaging optical system;

a displaying unit for displaying the image of the object picked-up by said image pickup element and for presenting at least one visual target point to an eye of an observer;

light source means for illuminating the pupil of the eye;

an area sensor for detecting a cornea reflection of said light source means and an image of the pupil of the eye;

a calculation unit for calculating the direction of the line of sight of the eye while the observer views the image of the object on said displaying unit from the positional relationship between the cornea reflection and the image of the pupil detected by said area sensor, said calculation unit calculating the direction of the line of sight using at least one parameter characteristic of the eye and relating to the image of the pupil and the cornea reflection, and obtaining the value of the parameter from the positional relationship between the image of the pupil and the cornea reflection on an imaging surface of said area sensor when the eye views said at least one visual target point; and an automatic focusing system, connected to said calculation unit and said imaging optical system, for performing a focusing operation of said imaging optical system, using the signal of a portion corresponding to the direction of the line of sight of the observer calculated by said calculation unit in a video signal of the image obtained by said image pickup element.

* * * * *

UNITED STATES PATENT AND TRADEMARK OFFICE
CERTIFICATE OF CORRECTION

PATENT NO. : 5,889,577

DATED : March 30, 1999

INVENTOR(S): YOSHIMI KOHAYAKAWA Page 1 of 2

It is certified that error appears in the above-identified patent and that said Letters Patent is hereby corrected as shown below:

COLUMN 2

Line 3, "focused" should read --focused on--.

COLUMN 12

Line 48, "of" (first occurrence) should be deleted.

COLUMN 13

Line 59, "spaced" should read --spaced at--.

COLUMN 16

Line 17, "cpmposed" should read --composed--.

UNITED STATES PATENT AND TRADEMARK OFFICE
CERTIFICATE OF CORRECTION

PATENT NO. : 5,889,577

DATED : March 30, 1999

INVENTOR(S): YOSHIMI KOHAYAKAWA

It is certified that error appears in the above-identified patent and that said Letters Patent is hereby corrected as shown below:

<u>COLUMN 21</u>

Line 33, "a" should read --an--.

Signed and Sealed this

Thirteenth Day of June, 2000

Attest:

Q. TODD DICKINSON

*Attesting Officer*          *Director of Patents and Trademarks*